US007301039B2

(12) United States Patent
Ramsden et al.

(10) Patent No.: US 7,301,039 B2
(45) Date of Patent: Nov. 27, 2007

(54) PROCESS FOR PREPARING CATIONIC RHODIUM COMPLEXES

(75) Inventors: James Andrew Ramsden, Cambridge (GB); Paul Henry Moran, Cambridge (GB)

(73) Assignee: Dow Global Technologies Inc., Midland, MI (US)

( * ) Notice: Subject to any disclaimer, the term of this patent is extended or adjusted under 35 U.S.C. 154(b) by 63 days.

(21) Appl. No.: 10/572,632

(22) PCT Filed: Sep. 30, 2004

(86) PCT No.: PCT/US2004/032255

§ 371 (c)(1),
(2), (4) Date: Mar. 17, 2006

(87) PCT Pub. No.: WO2005/032712

PCT Pub. Date: Apr. 14, 2005

(65) Prior Publication Data

US 2007/0004928 A1    Jan. 4, 2007

Related U.S. Application Data

(60) Provisional application No. 60/507,591, filed on Oct. 1, 2003.

(51) Int. Cl.
*C07F 15/00* (2006.01)
*B01J 31/00* (2006.01)
(52) U.S. Cl. .................... 556/14; 556/22; 502/154; 502/155
(58) Field of Classification Search .............. 556/22, 556/14; 502/154, 155
See application file for complete search history.

(56) References Cited

OTHER PUBLICATIONS

Brunner, Henri et al., "Enantioselective catalysis Part 129. A new rhodium(I) complex with a $\mu_2$-H bridged $Cp_2WH_2$ ligand". *Journal of Organometallic Chemistry*, 1999, pp. 346-350, 577.
Burckett-St.Laurent et al., Reactions of Metal Carbonyl Derivatives. 23.[1] Donor Behavior of [FeP$(C_6H_5)_2(CO)_2(\eta$-$C_5H_4R)$] (R=H, $CH_3$) toward Various Rhodium and Iridium Complexes and the Role of the Solvent in the Type of Product Formed. Reversible Uptake of Carbon Monoxide and Dihydrogen by the Nonclosed Trinuclear Species [M'{FeP$(C_6H_5)_2(CO)_2(\eta$-$C_5H_4R)$}$_2$]$^+$ (M'=Rh, Ir)$^{2n}$. *Inorganic Chemistry*, 1980, pp. 577-587, vol. 19, No. 3.
Burk, Mark J., et al., "Preparation and Use of $C_2$-Symmetric Bis(phospholanes):Production of $\alpha$-Amino Acid Derivatives via Highly Enantioselective Hydrogenation Reactions". *J. Am. Chem. Soc.* 1993, pp. 10125-10138, vol. 115, No. 22.
Cesarotti, E., et al., "Asymmetric Hydrogenation Catalyzed by Aminophosphine-Phosphiniterhodium Complexes Derived From Natural Aminoalcohols and X-ray Crystal Structure of (1,5-Cyclooctadiene)-(S)-N-(Diphenylphosphino)-2-Diphenylphosphinoxymethylpyrrolidinerhodium(I) Perchlorate". *Journal of Organometallic Chemistry*, 1983, pp. 79-91, 251.
Cobley, Christopher J. et al., "Highly Efficient Asymmetric Hydrogenation of 2-Methylenesuccinamic Acid Using a Rh-DuPHOS Catalyst". *Organic Process Research & Development*, 2003, pp. 407-411, vol. 7, No. 3.
Collman, James P. et al., "A Silica-Supported Rhodium Hydroformylation Catalyst: Evidence for Dinuclear Elimination". *J. Am. Chem. Soc.*, 1983, pp. 7288-7294, vol. 105, No. 25.
Crudden, Cathleen M. et al., "Rhodium bis-phosphine catalysts on mesoporous silica supports: new highly efficient catalysts for the hydrogenation of alkenes". *Chem. Commun.*, 2001, pp. 1154-1155.
Deschamps et al., "A New Type of Chelating Biphospholene," *Organometallics*, vol. 22, pp. 1356-1357 (2003).
Deschamps et al., "A New Type of Chelating Biphospholene," *Organometallics*, Supporting Information, pp. 1-13 (2003).
Falbe, Regitz, "Römpp Lexikon Chemie," 1998, Gerorg Thiem Verlag, Stuttgart-New York, p. 2700.
Holz, Jens, et al., "Hydroxyalkylphosphines in Asymmetric Hydrogenations," *Tetrahedron: Asymmetry*, 1995, pp. 1973-1988, vol. 6, No. 8.
Kunze, Christine, et al., "Calix[4]arene-based- Bis-phosphonites, Bis-phosphites, and Bis-O-acyl-phosphoites as Ligands in the Rhodium(i)-catalyzed Hydroformylation of 1-Octene". *Zeitschrift für anorganische und aligemeine Chemie*, Apr. 23, 2002, pp. 779-787, vol. 628, Issue 4—English Abstract Only.
Kunze, Christine et al., "Mono- and Binulear Rhodium and Platinum Complexes of 1,3,5-Trimethyl-1,3,5-triaza-$2\sigma^3\Lambda^3$-phosphorin-4,6-dionyloxy-substituted Calix[4]arenas". *Z. Anorg. Alig. Chem.*, 2002, pp. 545-552, 628.
Kyba, Evan P., Raymond E. Davis, Pedro N. Juri, and Kathleen R. Shirley. "Catalytic and Structural Studies of the Rhodium(I) Complexes of the norphos and renorphos Ligands". *Inorg. Chem.*, 1981, pp. 3616-3623, vol. 20, No. 11.
Miyano, Sotaro et al., "Axially Dissymmetric Bis(aminophosphine)s Derived from 2,2'-Diamino-1,1'-binaphthyl. Synthesis and Application to Rhodium(I)-Catalyzed Asymmetric Hydrogenations", *Bull. Chem. Soc. Jpn.*, vol. 57, pp. 2171-2176 (1984).
Polam, Jayapal Reddy et al., "Thiophene Complexes of the Platinum Group Metals. 2. Preparation and Characterization of Cationic Thiophene Complexes of [(cyclooctadiene)Ir][$BF_4$] and X-ray Crystal Structure of [($\eta^5$-2,5-dimethylthiophene)(cyclooctadiene)Fh][$BF_4$] and [(norbomadiene)Rh][$BF_4$]". *Organometallics*, 1993, pp. 3504-3509, vol. 12, No. 9.
Schrock, Richard R. et al., "Preparation and Properties of Some Cationic Complexes of Rhodium(I) and Rhodium (III)". *Journal of the American Chemical Society*, May 19, 1971, pp. 2397-2407, vol. 93, No. 10.
Selke, Rüdiger et al., "Asymmetric Hydrogenation—Influence of the Structure of Carbohydrate Derived Catalysts on the Relative Enantioselectivity $Q_{H/Me}$ Regarding Acid and Ester Substrates and its Inversion—Selectivity Increase in Water by Amphiphiles". *Tetrahedron*, 1996, pp. 15079-15102, vol. 52, No. 48.

(Continued)

*Primary Examiner*—Porfirio Nazario-Gonzalez

(57) ABSTRACT

The invention comprises a process for the preparation and isolation of a non-amorphous cationic rhodium complex having the formula: [Rh(ligand)$_m$(diolefin)]$^+$X$^-$, wherein the ligand is an enantiomerically enriched organic compound possessing one or two ligating phosphorus atoms.

56 Claims, No Drawings

OTHER PUBLICATIONS

Smith, Richard T. et al., "Rhodium Complexes of the Water-Soluble Phosphine $Ph_2PCH_2CH_2NMe_3^+$. Their Complexes with Hydride, Olefin, and Carbon Monoxide Ligands. Their use as Olefin Hydrogenation and Hydroformylation Catalysts in Aqueous Solution and in Aqueous/Organic Solvent Two-Phase Systems and Absorbed on a Cation-Exchange Resin". *Organometallics* 1983, pp. 1138-1144, vol. 2, No. 9.

Suarez, Andrés, et al., "Electronic Differences between Coordinating Functionalities of Chiral Phosphine-Phosphites and Effects in Catalytic Enantioselective Hydrogenation". *Organometallics* 2002, pp. 4611-4621, vol. 21, No. 22.

Schmid, Rudolf et al., "102. Axially Dissymmetric Bis(triaryl)phosphines in the Biphenyl Series: Synthesis of (6,6'-Dimethylbiphenyl-2,2'-diyl)bis(diphenylphosphine)(BIPHEMP) and Analogues, and their use in Rh(I)-Catalyzed Asymmetric Isomerizations of N,N-Diethylnerylamine". *Helvetica Chimica Acta*, 1988, pp. 897-929, vol. 71.

Schmid, Rudolf et al., "35. Axially Dissymmetric Diphosphines in the Biphenyl Series: Synthesis of (6,6'-Dimethoxybiphenyl-2,2'-diyl)bis(diphenylphosphine)(MeO-BIPHEP) and Analogues *via* and *ortho*-Lithiation/Iodination *Ullmann*-Reaction Approach", *Helvetica Chimica Acta*, 1991, pp. 370-389, vol. 74.

Thommen, Dr. Marc, "Design, Performance, Manufacture and Industrial Use of Chiral Ligands," *CHIRAL Europe 2003 Conference Proceedings* (4 pages).

Uehara, Akira and John C. Bailar, Jr. "Preparation and Catalytic Properties of Cationic Rhodium(I) Complexes Containing 2,2'-Bis(Diphenylphosphino)Biphenyl". *Journal of Organometallic Chemistry*, 1982, pp. 1-10, 239.

PROCESS FOR PREPARING CATIONIC RHODIUM COMPLEXES

This application is a 371 of PCT/US04/32255 filed Sep. 30, 2004 which claims benefit of application Ser. No. 60/507,591 filed Oct. 1, 2003.

BACKGROUND OF THE INVENTION

1. Field of the Invention

This invention relates to an improved process, suitable for operation on a commercial scale, for the preparation of cationic rhodium complexes of phosphorus-containing chiral ligands. In particular it relates to the preparation of rhodium complexes used as catalysts for asymmetric synthesis, in particular asymmetric hydrogenation.

2. Description of the Prior Art

The efficient production of chiral single enantiomer compounds is one of the most important challenges in modem fine chemical and pharmaceutical manufacturing. The asymmetric hydrogenation of substituted olefins by transition metal complexes modified with chiral phosphorus ligands is an exceptionally powerful method of introducing chirality in to a molecule. This is achieved by preferential binding to one face of the olefin by the transition metal/phosphorus ligand complex and subsequent hydrogenation gives rise to a product enriched in one stereoisomer. Asymmetric hydrogenation is particularly suitable to large-scale hydrogenation due to a variety of factors: use of sub-stoichiometric amounts of catalyst, the clean nature of the reaction and the availability of large-scale equipment. Many classes of phosphorus ligands and transition metal complexes have been developed for asymmetric olefin hydrogenation. Amongst the most effective catalysts are cationic rhodium chiral phosphorus ligand complexes. Their particular success is due to their high catalyst activity, productivity and enantioselectivity.

Fine chemicals and pharmaceutical intermediates hydrogenated by cationic rhodium chiral phosphorus ligand complexes are often complex multifunctional molecules and this complexity is frequently reflected in the requisite chiral phosphorus ligands which are similarly complex in structure and often made via multistep syntheses. As a consequence many of the most effective chiral phosphorus ligands are exceptionally difficult and costly to synthesise and the efficient formation of cationic rhodium phosphine complexes is a critical aspect of the economic viability of an asymmetric hydrogenation catalyst or its subsequent application in hydrogenation processes.

In principle cationic rhodium chiral phosphorus ligand complexes can be generated in two ways: 1) in-situ by mixing the chiral ligand and a suitable metal precursor or by 2) using a preformed complex. Using an in-situ formed catalyst has several distinct disadvantages: 1) many ligands are very oxygen sensitive and can be readily oxidised by poor handling; 2) in-situ catalyst formation introduces an extra process step; 3) in-situ generation of a catalyst can also give rise inconsistent results; 4) incorrect metal/ligand stoichiometry can adversely effect catalyst activity and selectivity. Such factors may limit applicability in pharmaceutical manufacturing from a regulatory as well as a technical viewpoint. However, use of a preformed complex can overcome these difficulties: 1) complexation of a sensitive ligand by a metal centre can stabilise the ligand; 2) preformed catalysts can be easily handled and introduced into a process avoiding an additional step and 3) a preformed catalyst will be a well defined and characterised species which gives more consistent results.

As asymmetric hydrogenation catalysts are most often used in the synthesis of high value active pharmaceutical ingredients, pharmaceutical intermediates and other fine chemicals it is of the utmost importance to guarantee the integrity of the catalyst and this can be readily achieved by use of preformed species. However, it is challenging to establish reliable and economic processes to prepare and isolate such cationic rhodium complexes in a form suitable for storage. This point is highlighted by the inability, to date, to form a crystalline cationic rhodium catalyst of adequate storage stability with the commercially available chiral ligand RoPHOS. Isolated solid cationic rhodium catalyst produced from RoPHOS undergoes spontaneous decomposition leading to loss of valuable catalyst and ligand (Conference Proceedings, Chiral Europe 2003, M. Thommen, Solvias A G).

The numerous chiral phosphorus ligand complexes described in the literature have given rise to a variety of synthetic routes to their corresponding cationic rhodium catalysts. The most common method for the preparation of cationic rhodium phosphorus complexes is the treatment of $[(1,5\text{-cyclooctadiene})_2Rh][X]$, where X is an anion and typically $[BF_4]^-$, $[PF_6]^-$, $[SbF_6]^-$, $[ClO_4]^-$, or $[OSO_2CF_3]^-$ with a requisite chiral phosphorus ligand. For representative examples see: *J. Am. Chem. Soc.* 1971, 73, 2397; *Helv. Chem. Acta.* 1991, 74, 370; *Organometallics* 2003, 93, 1356; *Organometallics* 2002, 21, 461 1; *J. Am. Chem. Soc.* 1993, 115, 10125. Where low polarity solvents are used to aid product recovery, inclusion of the metal-precursor in the product is a hazard due to the relative insolubility of $[(1,5\text{-cyclooctadiene})_2Rh][X]$ in low polarity solvents. Contamination of the chiral cationic rhodium catalyst with the achiral metal-precursor can reduce the overall stereoselectivity of the asymmetric hydrogenation. This problem can be overcome by using an excess of ligand, however, where expensive ligands are employed this option is undesirable. Moreover, further reaction of the preformed complex and excess ligand are a possibility giving rise to species less selective than the desired catalyst. Use of $[(1,5\text{-cyclooctadiene})_2Rh][X]$ in more polar solvents such as tetrahydrofuran often requires evaporation, trituration with an anti-solvent and crystallisation steps to obtain pure product.

In an alternative process, the chlorido precursor $[(1,5\text{-cyclooctadiene})RhCl]_2$ can be treated with salts such as $AgBF_4$, $AgPF_6$, $AgClO_4$, $AgSbF_6$, $NH_4PF_6$, $NaBF_4$, $NaSbF_6$ and $NaClO_4$ to abstract the chloride and treatment with a requisite phosphorus ligand can give rise to a cationic rhodium catalyst. For representative examples see: *J. Organometall. Chem.* 1999, 577, 346; *J: Organometall. Chem.* 1983, 251, 79, *Helv. Chim. Acta.* 1988, 71, 897; *Bull. Chem. Soc. Jpn.* 1984, 57, 2171; *Inorg. Chem.* 1980, 19, 577; *J. Organometall. Chem.* 1982, 239, 1. This route is disadvantageous for large scale applications as silver salts such as $AgBF_4$ and $AgSbF_6$ are expensive reagents. Furthermore, the AgCl generated must be removed by filtration before using the catalyst in subsequent reactions. Where salts such as $NaBF_4$ or $NH_4PF_6$ are used the chloride salts generated must be removed via an aqueous wash, thus adding additional separation and drying steps to remove salts and water. Also labile ligands such as phosphoramidites, phosphonites and phosphates are unsuitable for this method due to the reactivity towards moisture. Moreover, contamination of the cationic catalyst with chloride can be particularly detrimental to catalyst performance as highlighted by Cobley et al in *Organic Process Research & Development* 2003, 7, 407.

In another process where [(1,5-cyclooctadiene)Rh(acetylacetonate)] is treated with aqueous $HClO_4$, a cationic rhodium catalyst can be generated by addition of an appropriate phosphorus ligand, *Inorg. Chem.* 1981, 20, 3616. Yields can be variable using this method and also close examination of the reaction liquors by $^{31}P$-NMR reveals the presence of a variety species other than product thus limiting the maximum yield of the reaction. Use of the aqueous acids such $HClO_4$ limits the scope of chiral phosphorus ligands applicable in this method. Common chiral phosphorus ligands such as phosphites, phosphonites and phosphoramidites cannot be used with aqueous acids as the reaction conditions applied lead to decomposition of the ligand.

In a related method Schmutzler (*Z. Anorg. Allg. Chem.* 2002, 628, 545 and *Z. Anorg. Allg. Chem.* 2002, 628, 779) has shown direct reaction of [(1,5-cyclooctadiene)Rh(acetylacetonate)] with calixarene derived phosphites and biurets at −78° C. followed by subsequent reaction with ethereal $HBF_4$ can give rise to cationic rhodium phosphorus complexes, albeit in reduced yield and as an air- and moisture-sensitive form.

Another method of producing cationic rhodium phosphorus complexes is the reaction of [(norbomadiene)Rh(acetylacetonate)] with $Ph_3CBF_4$ and a suitable chiral phosphorus ligand, *J. Am. Chem. Soc.* 1983, 105, 7288. The applicability of this method in the industrial case is low due to the prohibitive cost of the reagent $Ph_3CBF_4$, furthermore the reaction required a reaction temperature of −78° C. and the product was only obtained after concentration, trituration and recrystallisation.

A common feature of the catalyst preparations described is the need for further manipulation of the crude reaction mixtures to isolate the catalyst. Most catalyst preparations result in a homogeneous solution whereby the catalyst must be precipitated from the reaction mixture by addition of an anti-solvent. Addition of anti-solvents commonly gives rise to rapid precipitation of microcrystalline or amorphous material with large surface areas. This is particularly disadvantageous as microcrystalline and amorphous materials are thermodynamically less stable than crystalline materials and can result in poor storability, poor handling ability and accelerated decomposition of the catalyst. In the industrial case, where catalysts are often purchased or prepared far in advance of their use, poor stability of the catalyst can have deleterious effects on the outcome of manufacturing campaigns and have significant financial implications due to loss of catalysts and compromised selectivities and yields. Often there is a need to recrystallise catalysts isolated via precipitation as the material is microcrystalline and of insufficient purity. This adds a further step and results in a reduced overall yield.

A manufacturing process for cationic rhodium catalysts that consistently produces high purity, crystalline material with a large range of phosphorus-containing ligands would be particularly advantageous. In contrast to the prior art the process of the present invention meets these requirements for industrial viability.

SUMMARY OF THE INVENTION

The invention comprises a process for the preparation and isolation of a non-amorphous cationic rhodium complex having the formula: $[Rh(ligand)_m(diolefin)]^+X^-$, wherein the ligand is an enantiomerically enriched organic compound possessing one or two ligating phosphorus atoms. The invention has general applicability to phosphorus-containing ligands from a wide variety of structural sub-types.

DETAILED DESCRIPTION OF THE PREFERRED EMBODIMENTS

The invention comprises a process for the preparation and isolation of a non-amorphous cationic rhodium complex of formula (1):

$$[Rh(ligand)_m(diolefin)]^+X^- \qquad (1)$$

wherein ligand represents an enantiomerically enriched organic compound possessing one or two ligating phosphorus atoms, and wherein m=2 when the ligand is monodentate and m=1 when the ligand is bidentate. The process of the invention comprises the following steps:
  (a) Dissolution of Rh(diolefin)(acac) in one or more ethereal solvents;
  (b) Addition of a fluorinated non-mineral acid HX and alcohol solvent or alcohol-containing solvent mixture, either simultaneously or sequentially, to form a soluble solvated complex of rhodium with one or more of the reaction solvents;
  (c) Addition of the ligand, either in solution in an organic solvent or neat;
  (d) Collection of the crystalline precipitate of complex (1).

Preferably, step (b) of the process involves simultaneous addition. More preferably, step (b) comprises addition of HX as a solution in an alcohol solvent or alcohol-containing solvent mixture.

Preferably, the diolefin used in the process is a cyclic diolefin. More preferably, the diolefin is selected from between 1,5-cyclooctadiene (COD) or 2,5-norbornadine (NBD). In the most preferred embodiment, the diolefin is COD. Alternatively, diolefin in formula (1) represents two molecules of an olefin selected from the group consisting of ethylene and $C_{5-10}$ cycloalkenes. The preferred fluorinated non-mineral acid HX of the process is a perflourinated non-mineral acid selected from the group consisting of $HBF_4$, $HPF_6$ and $HSbF_6$ or triflouromethanesulfonic acid. Most preferably, the fluorinated non-mineral acid HX is $HBF_4$.

In the preferred process, the ethereal solvents are selected from the group consisting of dialkyl ethers, tetrahydrofuran, 1,4-dioxane and 1,2-dimethoxyethane. In the case where dialkyl ethers are used as an ethereal solvent for the process of the invention, they are preferably selected from the group consisting of t-butyl methyl ether, diethyl ether, diisopropyl ether and di-n-butyl ether. Most preferably, the dialkyl ether is t-butyl methyl ether. Under an alternative embodiment, the dialkyl ether is in admixture with tetrahydrofuran. Preferably, the ratio of dialkyl ether:tetrahydrofuran ranges from about 10:1 to about 1:1. More preferably, the ratio of dialkyl ether:tetrahydrofuran ranges from about 6:1 to about 2:1.

Preferably, the alcohol solvent is a linear or branched $C_{1-6}$ alkanol, wherein the alkanol is selected from the group comprising methanol, ethanol, n-propanol, isopropanol, and 1-butanol. In the process of the invention, the organic solution used for dissolution of the ligand is selected from the group comprising ethereal solvents, non-polar hydrocarbon solvents and mixtures thereof In the ligands used in the process of the invention, the ligating phosphorus atom (or atoms) may either be in the form of a tertiary phosphine or may be covalently bonded to one or more heteroatoms. The description below of various embodiments of the invention is provided for the purpose of illustration, to present representative but non-limiting examples of suitable ligands. Numerous designs of bidentate and monodentate chiral phosphorus ligands have been reported and this continues to be a highly active area of scientific endeavor. For a recent comprehensive review, see Tang and Zhang, *Chem. Rev.*, 2003, 103, 3029.

When m=1 in complex (1) and the ligand is bidentate, in one embodiment of the invention the ligand is a diphosphine. The diphosphine may be a bisphosphacycle, preferably containing either two phospholane rings or two phosphetane rings. In the case of bisphospholanes, a well established class of ligands is represented by general formula (2), or the opposite enantiomer thereof, wherein X represents an organic or organometallic bridging radical, $R^1$ and $R^2$ are each independently H or an optionally substituted hydrocarbon group, provided that $R^1$ and $R^2$ are are not both H, the 3- and 4-positions of either or both phospholane rings optionally may be substituted with one or more non-interfering groups, and each phospholane ring may either be an isolated ring as depicted or embedded in a polycyclic ring system. Preferably, $R^1$ and $R^2$ are each independently $C_{1-20}$ alkyl, aryl or aralkyl. More preferably, $R^1=R^2=C_{1-20}$ alkyl or $R^1=R^2$=phenyl. In the case where $R^1=R^2=C_{1-20}$ alkyl, the alkyl is selected from the group consisting of methyl, ethyl, n-propyl, isopropyl, n-butyl, isobutyl, sec-butyl and t-butyl. The process of the present invention is applicable to in the preparation of complexes (1) in which the ligand is a hydroxylated variant of (2). For this embodiment it can be convenient to use a ligand precursor bearing an acid-labile hydroxyl protecting group, which is cleaved during formation of the rhodium complex.

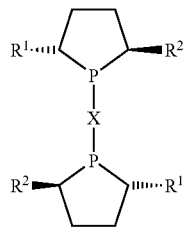

(2)

The preferred P—X—P bridging radical in the bisphospholane (2) is selected from a group consisting of formulae (3) to (8), each of which may be optionally substituted; n in (4) is in the range 0-5; X in (8) is either O or N-alkyl. More preferably P—X—P is either (3) or (4) in which n is 1. With respect to the backbone structures (3) to (8), it will be readily appreciated by those skilled in the art that through substitution of alternative backbone structures, it may be possible in order to obtain ligands that can be converted to rhodium complexes by the process of the present invention.

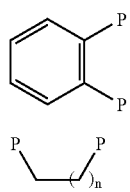

(3)

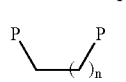

(4)

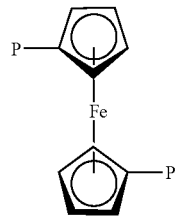

(5)

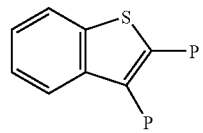

(6)

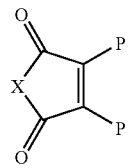

(7)

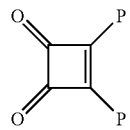

(8)

Alternative bisphospholane ligands that convertible to rhodium complexes by the process of the present invention are those containing two stereogenic phosphorus centers, including compound (9), the opposite enantiomer thereof and substituted analogues thereof.

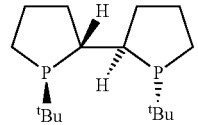

(9)

In the case of bisphosphetanes, a further embodiment of the process of the present invention employs a ligand represented by formula (10), or the opposite enantiomer thereof, wherein X represents an organic or organometallic bridging radical, $R^1$ and $R^2$ are each independently H or an optionally substituted hydrocarbon group, provided that $R^1$ and $R^2$ are are not both H, and the 3-position of either or both phosphetane rings optionally may be substituted with one or more non-interfering groups. Preferably X is 1,1'-ferrocenyl and $R^1$ and $R^2$ are each independently $C_{1-20}$ alkyl, aryl or aralkyl. More preferably, $R^1=R^2=C_{1-20}$ alkyl or $R^1=R^2$=phenyl. In the case where $R^1=R^2=C_{1-20}$ alkyl, the alkyl is selected from the group consisting of methyl, ethyl, n-propyl, isopropyl, n-butyl, isobutyl, sec-butyl and t-butyl.

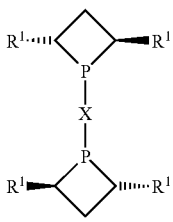

(10)

Yet another embodiment of the process of the invention utilizes a diphosphine ligand comprising an atropisomeric diphosphine containing two P(Ar)$_2$ groups, wherein Ar=phenyl, optionally substituted with one or more alkyl or alkoxy groups. Preferably, the atropisomeric diphosphine is a biaryldiphosphine in which the biaryl moiety may optionally be heteroaromatic. A preferred biaryldiphosphine of the invention is a BINAP ligand of formula (11), or the opposite enantiomer thereof. A representative heteroaromatic analogue is the diphosphine (12), or the opposite enantiomer thereof.

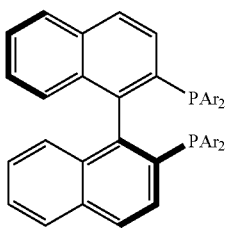

(11)

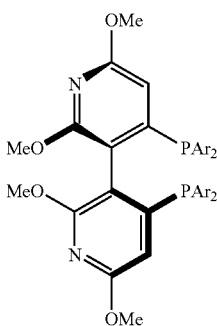

(12)

A further embodiment of the invention comprises a process wherein the diphosphine is a ligand of formula (13), or the opposite enantiomer thereof. Optionally, the [2,2']-paracyclophane backbone of (13) may be further substituted.

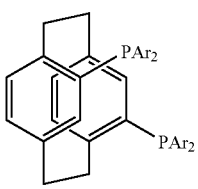

(13)

A further embodiment of the invention comprises a process wherein the ligand is a chiral ferrocene-based diphosphine. In addition to the bisphosphetane (10) wherein X=1, 1-ferrocenyl, there are several well established sub-classes of such diphosphines, as described by Tang and Zhang, ibid. The non-C$_2$-symmetric Josiphos-type ligands of Togni et al. (*J. Am. Chem. Soc.*, 1994, 116, 4062) provide the best known examples.

When m=1 in complex (1), at least one of the ligating phosphorus atoms in the ligand may be covalently bonded to one or more heteroatoms. In this embodiment of the invention, preferably both ligating phosphorus atoms are covalently bonded to one or more heteroatoms. More preferably, the ligand is selected from the group consisting of bisphosphites, bisphosphinites, bisphosphonites and bisphosphoramidites.

Yet another embodiment of the invention comprises a process wherein the ligand is a monophosphine and accordingly m=2 in complex (1). Preferably, the monophosphine ligand comprises a P-aryl phosphacycle. Still another embodiment of the invention comprises a process wherein the ligand is a phosphoramidite of formula (14), or the opposite enantiomer thereof, and accordingly m=2 in complex (1)

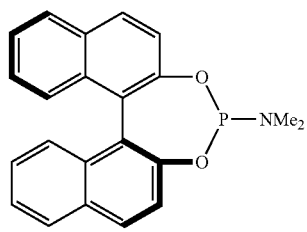

(14)

Throughout all embodiments of the invention, it is preferred that complex (1) be obtained in a crystalline form and that complex (1) is stable to storage, under an inert atmosphere at ambient temperature, for at least three (3) days. According to the preferred embodiment of the process of the invention, the ligand is enantiomerically enriched to at least 95% ee. More preferably, the ligand is enantiomerically enriched to at least 99% ee. Most preferably, the ligand is enantiomerically pure.

The following examples illustrate the present invention:

EXAMPLE 1

Synthesis of ((−)-1,2-Bis-((2R,5R)-2,5-dimethylphospholano)benzene)(1,5-cyclooctadiene) rhodium(I) tetrafluoroborate: [((R,R)-MeDuPHOS) Rh (COD)][BF$_4$]

A 10 liter jacketed glass vessel fitted with a programmable circulator, contact thermometer, over-head stirrer, reflux condenser, condenser circulator, bottom outlet valve, three addition ports, two membrane dosing pumps and a filter assembly with 10 liter receiver flask was connected to nitrogen/vacuum assembly and placed under an inert nitrogen atmosphere. The reactor was charged with 0.600 kg (1.934 mol) of (1,5-cyclooctadiene)(acetylacetonato) rhodium(I), 0.411 kg of degassed tetrahydrofuran and 1.708 kg of degassed t-butyl methyl ether. The reflux condenser temperature was set to 10° C. The vessel contents were stirred and heated via the programmable circulator to gentle reflux until all material was dissolved. A schlenk flask fitted with a side arm with an inline filter, connected to the reactor via a dosing pump, was charged with 0.726 kg of degassed propan-2-ol, 0.376 kg (2.322 mol) tetrafluoroboric acid diethyletherate was slowly added to the propan-2-ol under stirring whilst maintaining a temperature 35° C. or below. A second schlenk flask with a side arm and an in-line filter, connected to the reactor via a second membrane pump, was charged with 1.069 kg of degassed tetrahydrofuran and 0.593 kg (1.935 mol) of ((−)-1,2-bis((2R,5R)-2,5-dimethylphospholano)benzene) under stirring until all material had dissolved. The propan-2-ol solution of tetrafluoroboric acid diethyletherate was added continuously over 25 minutes to the reactor vessel, whist maintaining a gentle reflux, using a membrane dosing pump to give a transparent yellow/brown homogenous solution. The dosing pump line was rinsed with 3×20 ml of degassed propan-2-ol and the reactor contents stirred at reflux for approximately ~20 minutes. The solution of ((−)-1,2-bis((2R,5R)-2,5-dimethylphospholano)benzene) in degassed tetrahydrofuran was added continuously over ~22 minutes using a membrane dosing pump, whilst maintaining gentle reflux, and the pump lines rinsed with 3×20 ml or degassed tetrahydrofuran. Addition of the ((−)-1,2-bis((2R,5R)-2,5-dimethylphospholano)benzene) solution caused almost instant precipitation of deep red crystalline product. After addition of the ((−)-1,2-bis((2R,5R)-2,5-dimethylphospholano)benzene) solution was complete the vessel contents were stirred at reflux for ~26 mins before programming the vessel circulator to cool to ~−25° C. over six hours in a linear fashion. The vessel contents were transferred to the filter assembly under $N_2$ via the bottom outlet valve under a $N_2$ pressure. The reactor and the filter assembly were rinsed twice via the vessel with 2×1.25 kg of degassed propan-2-ol and the residual solvent removed under vacuum. The filter cake was finally rinsed with 3×0.384 kg of a degassed 3:2 tetrahydrofuran/t-butyl methyl ether solution and vacuum dried to constant weight. The reaction yielded 1.102 kg, 94.3% of ((−)-1,2-bis((2R,5R)-2,5-dimethylphospholano)benzene)(1,5-cyclooctadiene) rhodium(I) tetrafluoroborate.

$^{31}$P NMR (162 MHz, CDCl$_3$) δ77.1 ppm, doublet, $J_{Rh-P}$ 148.6 Hz

EXAMPLE 2

Synthesis of ((−)-1,2-Bis-((2R,5R)-2,5-diethylphospholano)benzene)(1,5-cyclooctadiene)rhodium(I) tetrafluoroborate: [((R,R)-EtDuPHOS) Rh (COD)] [BF$_4$]

A schlenk flask under nitrogen was charged with 1.5988 g (5.154 mmol) of (1,5-cyclooctadiene)(acetylacetonato) rhodium(I), 1.239 g dry, degassed tetrahydrofuran and 6.147 g of degassed t-butyl methyl ether and heated to 55° C. under stirring until all the material dissolved. A solution of 1.001 g (6.1848 mmol) of tetrafluoroboric acid diethyletherate in 1.918 g of degassed propan-2-ol was added dropwise via syringe over 10 mins to give a homogeneous yellow/brown solution. The resulting solution was stirred for a further 20 mins. A solution of 1.8687 g (5.154 mmol) (−)-1,2-bis((2R,5R)-2,5-diethylphospholano)benzene in 7.400 g of degassed t-butyl methyl ether was added dropwise over 10 minutes to give a red crystalline precipitate. The reaction was stirred for a further 20 minutes before cooling to −20° C. The reaction solvent was removed via syringe and the material washed with 2×1.48 g degassed t-butyl methyl ether and dried under vacuum to give 3.211 g, 97% yield of ((−)-1,2-bis((2R,5R)-2,5-diethylphospholano)benzene)(1,5-cyclooctadiene)rhodium(I) tetrafluoroborate.

$^{31}$P NMR (162 MHz, CDCl$_3$) δ70.4 ppm, doublet $J_{Rh-P}$ 148.7 Hz

EXAMPLE 3

Synthesis of ((+)-1,2-Bis-((2R,5R)-2.,-dimethylphospholano)ethane(1,5-cyclooctadiene)rhodium (I) tetrafluoroborate: [((R,R)-MeBPE) Rh (COD)] [BF$_4$]

A schlenk flask under nitrogen was charged with 6.00 g (19.356 mmol) of (1,5-cyclooctadiene)(acetylacetonato) rhodium(I), 4.656 g dry, degassed tetrahydrofuran and 23.082 g of degassed t-butyl methyl ether and heated to 55° C. under stirring until all the material dissolved. A solution of 3.76 g (23.22 mmol) of tetrafluoroboric acid diethyletherate in 7.20 g of degassed propan-2-ol was added dropwise via syringe over 10 mins to give a homogeneous yellow/brown solution. The resulting solution was stirred for a further 20 mins. A solution of 5 g (19.356 mmol) of 1,2-bis-((2R,5R)-2,5-dimethylphospholano)ethane in 22.2 g of degassed t-butyl methyl ether was added dropwise over 20 minutes to give an orange/red crystalline precipitate. The reaction was stirred for a further 20 minutes before cooling to −20° C. The reaction was filtered under nitrogen and dried under vacuum to give 10.19 g, 96.4% yield of (1,2-bis-((2R,5R)-2,5-dimethylphospholano)ethane)(1,5-cyclooctadiene) rhodium(I) tetrafluoroborate.

$^{31}$P NMR (162 MHz, CDCl$_3$) δ77.49 ppm, doublet $J_{Rh-P}$ 144.7 Hz

EXAMPLE 4

Synthesis of (1,2-Bis-((2S,5S)-2,5-diphenylphospholano)ethane)(1,5-cyclooctadiene)rhodium(I)tetrafluoroborate: [((R,R)-PhBPE) Rh (COD)][BF$_4$]

A schlenk flask under nitrogen was charged with 340 mg (1.096 mmol) of (1,5-cyclooctadiene)(acetylacetonato) rhodium(I), 445 mg dry, degassed tetrahydrofuran and 2.59 g of degassed t-butyl methyl ether and heated to 55° C. under stirring until all the material dissolved. A solution of 214 mg (1.322 mmol) of tetrafluoroboric acid diethyletherate in 392 mg of degassed propan-2-ol was added dropwise via syringe over 10 mins to give a homogeneous yellow/brown solution. The resulting solution was stirred for a further 30 mins. A solution of 556 mg (1.0975 mmol) of 1,2-bis-((2S,5S)-2,5-diphenylphospholano)ethane in 4.445 g of degassed tetrahydrofuran was added dropwise over 10 minutes to give an orange crystalline precipitate. The reaction was stirred for a further 30 minutes before cooling to room temperature. The reaction was filtered under nitrogen and the material washed with 3.925 g degassed propan-2-ol, 8.89 g degassed tetrahydrofuran and dried under vacuum to give 860 mg, 97.5% yield of (1,2-bis-((2S,5S)-2,5-diphenylphospholano)ethane)(1,5-cyclooctadiene)rhodium(I) tetrafluoroborate.

$^{31}$P NMR (162 MHz, CDCl$_3$) δ79.64 ppm, doublet $J_{Rh-P}$ 153.9 Hz

EXAMPLE 5

Synthesis of (1,1'-Bis-((2R,5R)-2,5-diisopropylphospholano)ferrocene)(1,5-cyclooctadiene) rhodium(I) tetrafluoroborate: [((R,R)-i-Pr-5-Fc) Rh (COD)][BF$_4$]

A schlenk flask under nitrogen was charged with 200 mg (0.6448 mmol) of (1,5-cyclooctadiene)(acetylacetonato) rhodium(I), 155 mg dry, degassed tetrahydrofuran and 769 mg of degassed t-butyl methyl ether and heated to 55° C. under stirring until all the material dissolved. A solution of 125 mg (0.7719 mmol) of tetrafluoroboric acid diethyletherate in 240 mg of degassed propan-2-ol was added dropwise via syringe over 10 mins to give a homogeneous yellow/brown solution. The resulting solution was stirred for a further 20 mins. A solution of 338.2 mg (0.6448 mmol) of 1,1'-bis((2R,5R)-2,5-diisopropylphospholano)ferrocene in 1.48 g of degassed t-butyl methyl ether was added dropwise over 10 minutes to give an orange crystalline precipitate. The reaction was stirred for a further 10 minutes before cooling to −20° C. The reaction solvent was removed via syringe and the material washed with 2×1.48 g degassed t-butyl methyl ether and dried under vacuum to give 507 mg, 96.9% yield of (1,1'-bis((2R,5R)-2,5-diisopropylphospholano)ferrocene)(1,5-cyclooctadiene)rhodium(I) tetrafluoroborate.

$^{31}$P NMR (162 MHz, CDCl$_3$) δ30.3 ppm, doublet J$_{Rh-P}$ 141.2 Hz

EXAMPLE 6

Synthesis of ((+)-1,1'-Bis-((2R,4R)-2,4-diethylphosphetano)ferrocene)(1,5-cyclooctadiene)rhodium(I) tetrafluoroborate: [((R,R)-EtFerroTANE) Rh (COD)][BF$_4$]

A schlenk flask under nitrogen was charged with 3.522 g (11.355 mmol) of (1,5-cyclooctadiene)(acetylacetonato) rhodium(I), 2.729 g dry, degassed tetrahydrofuran and 13.541 g of degassed t-butyl methyl ether and heated to 55° C. under stirring until all the material dissolved. A solution of 2.206 g (13.626 mmol) of tetrafluoroboric acid diethyletherate in 4.225 g of degassed propan-2-ol was added dropwise via syringe over 10 mins to give a homogeneous yellow/brown solution. The resulting solution was stirred for a further 20 mins. A solution of 5 g (11.355 mmol) of (+)-1,1'-bis-((2R,4R)-2,4-diethylphosphetano)ferrocene in 14.80 g of degassed t-butyl methyl ether was added dropwise over 10 minutes to give an orange crystalline precipitate. The reaction was stirred for a further 20 minutes before cooling to −20° C. The reaction was filtered under nitrogen and dried under vacuum to give 7.55 g, 91% yield of ((+)-1,1'-bis-((2R,4R)-2,4-diethylphosphetano)ferrocene)(1,5-cyclooctadiene)rhodium(I) tetrafluoroborate.

$^{31}$P NMR (162 MHz, CDCl$_3$) δ51.74 ppm, doublet J$_{Rh-P}$ 146.4 Hz

EXAMPLE 7

Synthesis of ((R)-(+)-2,2'-Bis-(diphenylphosphino)-1,1'-binaphthyl)(1,5-cyclooctadiene)rhodium(I) tetrafluoroborate: [((R)-BINAP) Rh (COD)][BF$_4$]

A schlenk flask under nitrogen was charged with 100 mg (0.322 mmol) of (1,5-cyclooctadiene)(acetylacetonato) rhodium(I), 68.5 mg dry, degassed tetrahydrofuran and 384.7 mg of degassed t-butyl methyl ether and heated to 55° C. under stirring until all the material dissolved. A solution of 62.6 mg (0.387 mmol) of tetrafluoroboric acid diethyletherate in 120 mg of degassed propan-2-ol was added dropwise via syringe over 10 mins to give a homogeneous yellow/brown solution. The resulting solution was stirred for a further 20 mins. A solution of 200.6 mg (0.322 mmol) (R)-(+)-2,2'-bis(diphenylphosphino)-1,1'-binaphthyl in 0.889 g of degassed tetrahydrofuran and 2.2 g of degassed t-butyl methyl ether was added dropwise over 10 minutes to give an orange/red crystalline precipitate. The reaction was stirred for a further 20 minutes before cooling to −20° C. The reaction solvent was removed via syringe and the material washed with 2×1.48 g degassed t-butyl methyl ether and dried under vacuum to give 292 mg, 99% yield of ((R)-(+)-2,2'-bis(diphenylphosphino)-1,1'-binaphthyl)(1,5-cyclooctadiene)rhodium(I) tetrafluoroborate.

$^{31}$P NMR (162 MHz, CDCl$_3$) δ26.6 ppm, doublet J$_{Rh-P}$ 146.8 Hz

EXAMPLE 8

Synthesis of ((R)-(−)-4,12-Bis-(diphenylphosphino)-[2.2]-paracyclophane)(1,5-cyclooctadiene)rhodium (I) tetrafluoroborate: [((R)-PhanePhos) Rh (COD)][BF$_4$]

A schlenk flask under nitrogen was charged with 50 mg (0.1612 mmol) of (1,5-cyclooctadiene)(acetylacetonato) rhodium(I), 34.25 mg dry, degassed tetrahydrofuran and 192.4 mg of degassed t-butyl methyl ether and heated to 55° C. under stirring until all the material dissolved. A solution of 31.3 mg (0.1934 mmol) of tetrafluoroboric acid diethyletherate in 60 mg of degassed propan-2-ol was added dropwise via syringe over 10 mins to give a homogeneous yellow/brown solution. The resulting solution was stirred for a further 25 mins. A solution of 92.95 mg (0.1612 mmol) (R)-(−)-4,12-bis(diphenylphosphino)-[2.2]-paracyclophane in 1.78 g of degassed tetrahydrofuran and 2.2 g of degassed t-butyl methyl ether was added dropwise over 10 minutes to give an orange/red crystalline precipitate. The reaction was stirred for a further 20 minutes before cooling to −20° C. The reaction solvent was removed via syringe and the material washed with 2×1.48 g degassed t-butyl methyl ether and dried under vacuum to give 134 mg, 95% yield of ((R)-(−)-4,12-bis(diphenylphosphino)-[2.2]-paracyclophane)(1,5-cyclooctadiene)rhodium(I) tetrafluoroborate.

$^{31}$P NMR (162 MHz, CDCl$_3$) δ33.3 ppm, doublet J$_{Rh-P}$ 147 Hz

EXAMPLE 9

Synthesis of (Bis-((R)-(−)-(3,5-Dioxa-4-phosphacyclohepta[2,1-a:3,4-a']dinaphthalen-4-yl)dimethylamine))(1,5-cyclooctadiene)rhodium(I) tetrafluoroborate: [((R)-Monophos)$_2$ Rh (COD)][BF$_4$]

A schlenk flask under nitrogen was charged with 100 mg (0.322 mmol) of (1,5-cyclooctadiene)(acetylacetonato) rhodium(I), 68.5 mg dry, degassed tetrahydrofuran and 384.7 mg of degassed t-butyl methyl ether and heated to 55° C. under stirring until all the material dissolved. A solution of 62.6 mg (0.387 mmol) of tetrafluoroboric acid diethyletherate in 120 mg of degassed propan-2-ol was added dropwise via syringe over 10 mins to give a homogeneous yellow/brown solution. The resulting solution was stirred for a further 20 mins. A solution of 231.6 mg (0.644 mmol)

(R)-(-)-(3,5-dioxa-4-phospha-cyclohepta[2,1-a;3,4-a']dinaphthalen-4-yl)dimethylamine in 1.33 g of degassed tetrahydrofuran and 2.2 g of degassed t-butyl methyl ether was added dropwise over 10 minutes to give an orange/yellow crystalline precipitate. The reaction was stirred for a further 20 minutes before cooling to −20° C. The reaction solvent was removed via syringe and the material washed with 2×1.48 g degassed t-butyl methyl ether and dried under vacuum to give 281 mg, 87% yield of (bis-((R)-(-)-(3,5-dioxa-4-phospha-cyclohepta[2,1-a;3,4-a']dinaphthalen-4-yl)dimethylamine))(1,5-cyclooctadiene)rhodium(I) tetrafluoroborate.

$^{31}$P NMR (162 MHz, CDCl$_3$) δ138 ppm, broad doublet of multiplets

EXAMPLE 10

Synthesis of ((R)-2,2',6,6'-Tetramethoy-4,4'-bis(di(3,5-xylyl)phosphino)-3,3'-bipyridine)(1,5-cyclooctadiene)rhodium(I) tetrafluoroborate: [(CTH-(R)-Xylyl-P-Phos) Rh (COD)][BF$_4$]

A Schlenk flask under nitrogen was charged with 42 mg (0.135 mmol) of (1,5-cyclooctadiene)(acetylacetonato)rhodium(I), 100 µl dry, degassed tetrahydrofuran and 200 µl of degassed t-butyl methyl ether and heated to 55° C. under stirring until all the material dissolved. A solution of 18 µl (0.132 mmol) of tetrafluoroboric acid diethyletherate in 100 µl of degassed propan-2-ol was added dropwise via syringe over 10 mins to give a homogeneous yellow/brown solution. The resulting solution was stirred for a further 25 mins. A solution of 102 mg (0.135 mmol) ((R)-2,2',6,6'-Tetramethoxy-4,4'-bis(di(3,5-xylyl)phosphino)-3,3'-bipyridine) in 0.5 ml of degassed tetrahydrofuran and 2 ml of degassed t-butyl methyl ether was added dropwise over 30 minutes to give an orange/red crystalline precipitate. The reaction was stirred for a further 20 minutes before cooling to room temperature. A further 8 ml of degassed t-butyl methyl ether was added dropwise The mixture was cooled to −20° C., the reaction solvent was removed via syringe and the material was dried under vacuum to give 66 mg, 46% yield of ((R)-2,2',6,6'-Tetramethoxy-4,4'-bis(di(3,5-xylyl)phosphino)-3,3'-bipyridine)(1,5-cyclooctadiene)rhodium(I) tetrafluoroborate.

$^{31}$P NMR (162 MHz, CDCl$_3$) δ24.7 ppm, doublet J$_{Rh-P}$ 143 Hz

EXAMPLE 11

Synthesis of ((1S,1S',2R,2R')-1,1'-Di-t-butyl-[2,2']diphospholane)(1,5-cyclooctadiene)rhodium(I) tetrafluoroborate: [((S,S,R,R)-TangPhos) Rh (COD)][BF$_4$]

A Schlenk flask under nitrogen was charged with 121 mg (0.395 mmol) of (1,5-cyclooctadiene)(acetylacetonato)rhodium (I), 300 µl dry, degassed tetrahydrofuran and 600 µl of degassed t-butyl methyl ether and heated to 55° C. under stirring until all the material dissolved. A solution of 54 µl (0.397 mmol) of tetrafluoroboric acid diethyletherate in 100 µl of degassed propan-2-ol was added dropwise via syringe over 10 mins to give a homogeneous yellow/brown solution. The resulting solution was stirred for a further 25 mins. A solution of 113 mg (0.135 mmol) (1S,1S',2R,2R'-1,1'-Di-t-butyl-[2,2']diphospholane in 1 ml of degassed tetrahydrofuran and 2 ml of degassed t-butyl methyl ether was added dropwise over 1 h to give an orange/red crystalline precipitate. The reaction was stirred for a further 20 minutes before cooling to room temperature then cooling in an ice water bath. The product was collected in a Schlenk filter and washed with a further 2×2 ml of degassed t-butyl methyl ether. The material was dried under vacuum to give 166 mg, 72% yield of ((1S,1S',2R,2R')-1,1'-Di-t-butyl-[2,2']diphospholane)(1,5-cyclooctadiene)rhodium(I) tetrafluoroborate.

$^{31}$P NMR (162 MHz, CDCl$_3$) δ97.7 ppm, doublet J$_{Rh-P}$ 143 Hz

EXAMPLE 12

Synthesis of {(1,2-Bis[(2S,5S)-2,5-dimethyl-(3S,4S)-3,4-dihydroxyphosphalano]benzene}(1,5-cyclooctadiene)rhodium(I) tetrafluoroborate, with in-situ deprotection of the ligand precursor A Schlenk flask under nitrogen was charged with 70 mg (0.226 mmol) of (1,5-cyclooctadiene)(acetylacetonato)rhodium(I), 200 µl dry, degassed tetrahydrofuran and 400 µl of degassed t-butyl methyl ether and heated to 55° C. under stirring until all the material dissolved. A solution of 25 µl (0.13 mmol) of tetrafluoroboric acid diethyletherate in 100 µl of degassed propan-2-ol was added dropwise via syringe over 10 mins to give a homogeneous yellow/brown solution. The resulting solution was stirred for a further 30 mins. A solution of 101 mg (0.224 mmol) (S,S,S,S)-MeKetalPhos in 0.5 ml of degassed tetrahydrofuran and 2 ml of degassed t-butyl methyl ether was added dropwise over 1 h to give an orange/red crystalline precipitate. A further 2 ml of t-butyl methyl ether was added dropwise. The reaction was stirred for a further 60 minutes before cooling to room temperature then cooling in an ice water bath. The supernatant liquid was removed and the residue was dried under vacuum to give the product as a red powder 55 mg, 63% yield of {(1,2-Bis[(2S,5S)-2,5-dimethyl-(3S,4S)-3,4-dihydroxyphosphalano]benzene}(1,5-cyclooctadiene)rhodium(I) tetrafluoroborate.

$^{31}$P NMR (162 MHz, d$_4$-MeOH) δ77.6 ppm, doublet J$_{Rh-P}$ 152 Hz

The invention claimed is:

1. A process for preparation and isolation of a non-amorphous cationic rhodium complex of formula (1), wherein ligand represents an enantiomerically enriched organic compound possessing one or two ligating phosphorus atoms, and wherein m=2 when the ligand is monodentate and m=1 when the ligand is bidentate, which comprises the following steps:

(a) Dissolution of Rh(diolefin)(acac) in one or more ethereal solvents;
    (b) Addition of a fluorinated non-mineral acid HX and alcohol solvent or alcohol-containing solvent mixture, either simultaneously or sequentially, to form a soluble solvated complex of rhodium with one or more of the reaction solvents;
    (c) Addition of the ligand, either in solution in an organic solvent or neat;
    (d) Collection of the crystalline precipitate of complex (1)

$$[Rh(ligand)_m(diolefin)]^+X^- \qquad (1).$$

2. A process according to claim 1, wherein step (b) comprises simultaneous addition of HX and alcohol solvent or alcohol-containing solvent mixture.

3. A process according to claim 2, wherein step (b) comprises addition of HX as a solution in an alcohol solvent or alcohol-containing solvent mixture.

4. A process according to claim 1, wherein step (b) comprises sequential addition, in either order, of HX and alcohol solvent or alcohol-containing solvent mixture.

5. A process according to claim 1, wherein the diolefin is a cyclic diolefin.

6. A process according to claim 5, wherein the diolefin is either 1,5-cyclooctadiene (COD) or 2,5-norbornadine (NBD).

7. A process according to claim 6, wherein the diolefin is COD.

8. A process according to claim 1, wherein diolefin represents two molecules of an olefin selected from the group consisting of ethylene and $C_{5-10}$ cycloalkenes.

9. A process according to claim 1, wherein HX is a perflourinated non-mineral acid.

10. A process according to claim 9, wherein HX is selected from the group consisting of $HBF_4$, $HPF_6$, $HSbF_6$ and $CF_3SO_3H$.

11. A process according to claim 10, wherein HX is $HBF_4$.

12. A process according to claim 1, wherein ethereal solvents are selected from the group consisting of dialkyl ethers, tetrahydrofuran, 1,4-dioxane and 1,2-dimethoxyethane.

13. A process according to claim 12, wherein dialkyl ethers are selected from the group consisting of t-butyl methyl ether, diethyl ether, diisopropyl ether and di-n-butyl ether.

14. A process according to claim 13, wherein a dialkyl ether is in admixture with tetrahydrofuran.

15. A process according to claim 14, wherein the ratio of diallyl ether:tetrahydrofuran ranges from about 10:1 to about 1:1.

16. A process according to claim 15, wherein the ratio of dialkyl ether:tetrahydrofuran ranges from about 6:1 to about 2:1.

17. A process according to claim 16, wherein the dialkyl ether is t-butyl methyl ether.

18. A process according to claim 1, wherein the alcohol is a linear or branched $C_{1-6}$ alkanol.

19. A process according to claim 18, wherein the alkanol is selected from the group consisting of methanol, ethanol, n-propanol, isopropanol, and 1-butanol.

20. A process according to claim 1, wherein the organic solution used for dissolution of ligand is selected from the group consisting of ethereal solvents, non-polar hydrocarbon solvents and mixtures thereof.

21. A process according to claim 1, wherein m=1.

22. A process according to claim 21, wherein the ligand is a diphosphine.

23. A process according to claim 22, wherein the diphosphine is a bisphosphacycle.

24. A process according to claim 23, wherein the bisphosphacycle is a bisphospholane.

25. A process according to claim 24, wherein the bisphosphacycle is a bisphospholane according to formula (2), or the opposite enantiomer thereof, wherein X represents an organic or organometallic bridging radical, $R^1$ and $R^2$ are each independently H or an optionally substituted hydrocarbon group, provided that $R^1$ and $R^2$ are not both H, and the 3- and 4-positions of either or both phospholane rings optionally may be substituted with one or more non-interfering groups

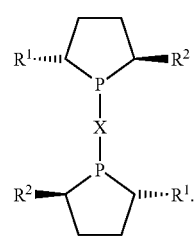

26. A process according to claim 25 wherein P—X—P in the bisphospholane is selected from a group consisting of formulae (3) to (8), each of which may be optionally substituted; n in (4) is in the range 0-5; X in (8) is either O or N-alkyl 27. A process according to claim 26, wherein P—X—P is of formula (3).

28. A process according to claim 26, wherein P—X—P is of formula (4) and n 1.

29. A process according to claim 26, wherein P—X—P is of formula (5).

30. A process according to claim 24, wherein the bisphosphacycle is a bisphospholane according to formula (9), the opposite enantiomer thereof and substituted analogues thereof.

31. A process according to claim 23, wherein the bisphosphacycle is a bisphosphetane of formula (10), wherein X represents an organic or organometallic bridging radical, $R^1$ and $R^2$ are each independently H or an optionally substituted hydrocarbon group, provided that $R^1$ and $R^2$ are are not both H, and the 3-position of either or both phosphetane rings optionally may be substituted with one or more non-interfering groups

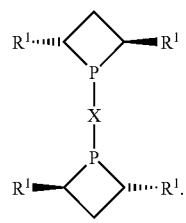

(10)

32. A process according to claim 31, wherein X is 1,1'-ferrocenyl.

33. A process according any of claims 25-29 or 31-32, wherein $R^1$ and $R^2$ are each independently $C_{1-20}$ alkyl, aryl or aralkyl.

34. A process according to claim 33, wherein $R^1=R^2=C_{1-20}$ alkyl.

35. A process according to claim 34, wherein alkyl is selected from the group consisting of methyl, ethyl, n-propyl, isopropyl, n-butyl, isobutyl, sec-butyl and t-butyl.

36. A process according to claim 33, wherein $R^1=R^2=$phenyl.

37. A process according to claim 19, wherein the diphosphine is an atropisomeric diphosphine containing two $P(Ar)_2$ groups, wherein Ar=phenyl, optionally substituted with one or more alkyl or alkoxy groups.

38. A process according to claim 32, wherein the diphosphine is a biaryldiphosphine.

39. A process according to claim 33, wherein the biaryldiphosphine is a BINAP ligand of formula (11), or the opposite enantiomer thereof

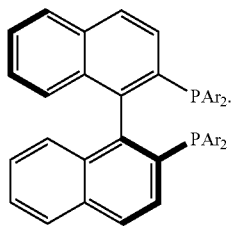

(11)

40. A process according to claim 38, wherein the biaryl moiety is heteroaromatic.

41. A process according to claim 32, wherein the diphosphine is a PHANEPHOS ligand of formula (13), or the opposite enantiomer thereof

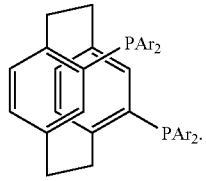

(13)

42. A process according to claim 21, wherein at least one of the ligating phosphorus atoms in the ligand is covalently bonded to one or more heteroatom.

43. A process according to claim 42, wherein both ligating phosphorus atoms are covalently bonded to one or more heteroatoms.

44. A process according to claim 43, wherein the ligand is selected from the group consisting of bisphosphites, bisphosphinites, bisphosphonites and bisphosphoramidites.

45. A process according to claim 1, wherein m=2.

46. A process according to claim 45, wherein the ligand is a monophosphine.

47. A process according to claim 46, wherein the phosphine is a P-aryl phosphacycle.

48. A process according to claim 45, wherein the ligating phosphorus atom in the ligand is covalently bonded to one or more heteroatoms.

49. A process according to claim 48, wherein the ligand is a phosphoramidite.

50. A process according to claim 49, wherein the phosphoramidite is of formula (14) or the opposite enantiomer thereof

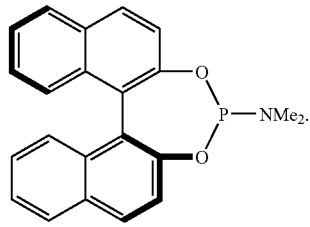

(14)

51. A process according to claim 1, wherein the complex (1) is prepared directly from a ligand precursor containing one or more acid-labile hydroxyl protecting groups, which are removed during complex formation.

52. A process according to claim 1, wherein the complex (1) is obtained is in a crystalline form.

53. A process according claim 1, wherein the complex (1) is stable to storage, under an inert atmosphere at ambient temperature, for at least three (3) days.

54. A process according the claim 1, wherein the ligand is enantiomerically enriched to at least 95% ee.

55. A process according the claim 54, wherein the ligand is enantiomerically enriched to at least 99% ee.

56. A process according to claim 55, wherein the ligand is enantiomerically pure.

* * * * *